United States Patent
Van Der Heijden et al.

(10) Patent No.: US 10,597,358 B2
(45) Date of Patent: Mar. 24, 2020

(54) SYNTHESIS OF CARBAMATE OR UREA COMPOUNDS

(71) Applicant: Nederlandse Organisatie voor toegepast-natuurwetenschappelijk onderzoek TNO, The Hague (NL)

(72) Inventors: Antonius Eduard Dominicus Maria Van Der Heijden, The Hague (NL); Erik Van Geest, The Hague (NL); Jos Johan Matthijs Hugo Van Den Elshout, The Hague (NL)

(73) Assignee: Nederlandse Organisatie voor toegepast-natuurwetenschappelijk onderzoek TNO, The Hague (NL)

( * ) Notice: Subject to any disclaimer, the term of this patent is extended or adjusted under 35 U.S.C. 154(b) by 0 days.

(21) Appl. No.: 15/544,165

(22) PCT Filed: Jan. 18, 2016

(86) PCT No.: PCT/NL2016/050042
§ 371 (c)(1),
(2) Date: Jul. 17, 2017

(87) PCT Pub. No.: WO2016/114670
PCT Pub. Date: Jul. 21, 2016

(65) Prior Publication Data
US 2018/0009743 A1    Jan. 11, 2018

(30) Foreign Application Priority Data

Jan. 16, 2015  (EP) .................................. 15151464
Jan. 29, 2015  (NL) .................................. 1041160

(51) Int. Cl.
| | | |
|---|---|---|
| C07C 273/18 | (2006.01) | |
| B01J 31/02 | (2006.01) | |
| C07C 269/04 | (2006.01) | |
| C07C 271/28 | (2006.01) | |
| C07C 271/58 | (2006.01) | |
| C07C 275/28 | (2006.01) | |

(52) U.S. Cl.
CPC ..... *C07C 273/1836* (2013.01); *B01J 31/0251* (2013.01); *B01J 31/0265* (2013.01); *B01J 31/0277* (2013.01); *B01J 31/0284* (2013.01); *C07C 269/04* (2013.01); *C07C 271/28* (2013.01); *C07C 271/58* (2013.01); *C07C 273/1809* (2013.01); *C07C 273/1845* (2013.01); *C07C 275/28* (2013.01)

(58) Field of Classification Search
None
See application file for complete search history.

(56) References Cited

FOREIGN PATENT DOCUMENTS

| EP | 0083096 A2 | | 7/1983 |
|---|---|---|---|
| JP | 2011111433 | * | 6/2011 |
| JP | 2011111433 A | | 6/2011 |
| WO | 2006068594 A1 | | 6/2006 |

OTHER PUBLICATIONS

Buysch ("Carbonic Esters" Ullmann's Encyclopedia of Industrial Chemistry, first published on Jun. 15, 2000, p. 45-71, downloaded from https://onlinelibrary.wiley.com/doi/10.1002/14356007.a05_197, on May 21, 2018) (Year: 2000).*
Jager ("Carbamates and Carbamoyl Chlorides" Ullmann's Encyclopedia of Industrial Chemistry, first published on Jun. 15, 2000, p. 553-560, downloaded from https://onlinelibrary.wiley.com/doi/10.1002/14356007.a05_051 on May 21, 2018) (Year: 2000).*
McQuarrie ("Le Chatelier's Principle Is Used to Predict the Direction of the Shift in a Chemical Reaction Displaced from Equilibrium" General Chemistry, Fourth Edition, 2011, p. 705-717, see whole document) (Year: 2011).*
Lee ("The direct conversion of carbamates to ureas using aluminum amides" Tetrahedron, 60, 2004, p. 3439-3443) (Year: 2004).*
Boers ("Lifetime Prediction of EC, DPA, Akardite II and MNA Stabilized Triple Base Propellants, Comparison of Heat Generation Rate and Stabilizer Consumption" Propellants, Explosives, Pyrotechnics, 30, No. 5, 2005, p. 356-362) (Year: 2005).*
English Language Translation of Wang ("Synthesis of Methyl N-Phenyl Carbamate Catalyzed by Ionic Liquid and 1,1,3,3-Tetramethylguanidine", Petrochemical Technology (Shiyou Huagong), vol. 37, 2008, p. 1255-1259) (Year: 2008).*
Elageed ("BmimOAc ionic liquid: A highly efficient catalyst for synthesis of 3-aryl-2-oxazolidinones by direct condensation of 2-(arylamino)alcohols with diethyl carbonate" J. Mol. Cat. A: Chemical, 408, 2015, p. 271-277) (Year: 2015).*
Shaik ("Organic Carbonates" Chem. Rev. 1996, 96, p. 951-976) (Year: 1996).*
Li ("Ru-catalyzed hydrogenation of 3,5-diketo amides: simultaneous control of chemo- and enantioselectivity" Chem. Commun., 2012, 48, p. 8976-8978, including SI p. S1-S114) (Year: 2012).*
Sigma Aldrich page for THF, downloaded from https://www.sigmaaldrich.com/chemistry/solvents/tetrahydrofuran-center.html on Jun. 21, 2019 (Year: 2019).*
Sigma Aldrich page for dioxane, downloaded from https://www.sigmaaldrich.com/catalog/product/sial/296309?lang=en&region=US on Jun. 21, 2019 (Year: 2019).*
Wang Na, et al.; "Synthesis of Methyl N-Phenyl Carbamate Catalyzed by Ionic Liquid and 1,1,3,3-Tetramethylguanidine"; Petrochemical Technology (Shiyou Huagong), vol. 37( 12), 2008, pag. 1255-1259.
Xianlei Fu, et al.; "N-heterocyclic carbomethoxylation catalyzed by ionic liquids in the presence of dimethyl carbonate"; Cat. Comm., vol. 10, 2009, pag. 665-668.
Hancheng Zhou, et al.; "Synthesis of carbamates from aliphatic amines and dimethyl carbonate catalyzed by acid functional ionic liquids"; J. Mol. Cat. A: Chem.; vol. 271, 2007, pag. 89-92.
Tianlong Sima, et al.; "The synthesis of carbamates from reactions of primary and secondary aliphatic amines with dimethyl carbonate in ionic liquids"; Tetrahedron Lett., vol. 43, 2002, pag. 8145-8147.

(Continued)

*Primary Examiner* — Amy C Bonaparte
(74) *Attorney, Agent, or Firm* — Verrill Dana, LLP

(57) ABSTRACT

The invention pertains to the synthesis of carbamate and urea compounds. In particular the invention is directed to the synthesis of carbamate and urea compounds which may be used in the production of compounds that are used to stabilize nitrocellulose. The method of the invention comprises preparing a carbamate or urea derivative comprising reacting an amine and a carbonate or carbamate in the presence of an ionic liquid.

16 Claims, No Drawings

(56) References Cited

OTHER PUBLICATIONS

Sunitha, Sadula et al., An efficient and ehemoselective Brønsted acidic ionic liquid-catalyzed N-Boc protection of amines, Tetrahedron Letters 49 (2008) 2527-2532.

Macneil, Stephen L., et al., Anionic N-Fries Rearrangment of N-Carbamoyl Diarylamines to Anthranilamides. Methodology and Application to Acridone and Pyranoacridone Alkaloids, Organic Letters, 2006, vol. 8, No. 6, 1133-1136.

Velavan A., et al. Unsymmetrical tetrasubstituted ureas from tertiary carbamoylimidazole: activation by AlMe3. Org. Biomol. Chem., 10, 6420-6431 (2012).

International Union of Pure and Applied Chemistry (IUPAC). IUPAC Compendium of Chemical Terminology Gold Book v. 2.3.3, p. 1486 (2014).

Boers, M et al., "Lifetime Prediction of EC, DPA, Akardite II and MNA Stabilized Triple Base Propellants, Comparison of Heat Generation Rate and Stabilizer Consumption", Propellants, Explosives, Pyrotechnics, vol. 30, Issue 5, pp. 314-385 Oct. 2005 doi: 10.1002/prep.200500026.

Buysch, HJ et al., "Carbonic Esters", Ullmann's Encyclopedia of Industrial Chemistry, 2012, Article No. a05_197, vol. 7, pp. 45-72. doi: 10.1002/14356007.a05_197.

Jager, P. et al., "Carbamates and Carbamoyl Chlorides", Ullmann's Encyclopedia of Industrial Chemistry, 2012, Article a05_051, vol. 6, pp. 553-560. doi: 10.1002/14356007.a05_051.

Lee, S.H. et al., "The direct conversion of carbamates to ureas using aluminum amides", Tetrahedron, vol. 60, Issue 15, Apr. 5, 2004, pp. 3439-3443. doi: 10.1016/j.tet.2004.02.034.

McQuarrie, D.A. et al., "General Chemistry" Fourth Edition, University Science Books, Wilsted & Taylor Publishing Services, 2011 University Science Books, 16 pages. ISBN 978-1-891389-60-3 Softcover Print Edition ISBN 978-1-891389-90-0 Digital E-book Edition.

\* cited by examiner

SYNTHESIS OF CARBAMATE OR UREA COMPOUNDS

The invention pertains to the synthesis of carbamate and urea compounds. In particular the invention is directed to the synthesis of carbamate and urea compounds which may be used in the production of compounds that are used to stabilize nitrocellulose.

Nitrocellulose is used as a propellant in ammunition and is made by the nitration of cellulose. Due to the high content of nitrate esters, nitrocellulose is intrinsically thermodynamically unstable. The nitrate esters decompose over time into RO- and $NO_2$-radicals (B. Vogelsanger, *Chimia* 2004, 58, 401-408). These radicals catalyze further decomposition of nitrocellulose. The decomposition of nitrocellulose is therefore classified as autocatalytic, which means that decomposition of nitrocellulose may lead to a runaway reaction resulting in self-ignition of the nitrocellulose (J. Rychlý et al., *J. Therm. Anal. Calorim.* 2012, 107, 1267-1276).

The decomposition of nitrocellulose may be slowed down by using stabilizers as additives. These stabilizers scavenge radicals and/or protons, thereby limiting the autocatalytic reaction and preventing a runaway reaction. Stabilizers are typically classified into the class of aromatic amines or into the class of aromatic urea derivatives. The aromatic urea derivatives comprise of symmetric alkyl-aryl substituted ureas and unsymmetric diaryl substituted ureas. Typical examples of the symmetric alkyl-aryl substituted ureas are Centralite I (diethyl-N,N'-diphenylurea) and Centralite II (dimethyl-N,N'-diphenylurea). Typical examples of unsymmetric diaryl substituted ureas are Akardite I (N',N'-diphenylurea) and Akardite II (N-methyl-N',N'-diphenylurea).

Decomposition or degradation of nitrocellulose is sometimes also referred to as ageing. Ammunition and thus the nitrocellulose comprised therein has to meet certain standards. The performance requirements for NATO ammunition are set forth in Standardization Agreement (STANAG) 4582 (NATO, 2004. STANAG 4582 (Edition 1)—Ratification Draft 1—Explosives, nitrocellulose based propellants, stability test procedure and requirements using heat flow calorimetry), which is incorporated herein by reference. STANAG 4582 also describes methods to determine the performance of the stabilizer in slowing down the ageing of the propellant.

S. Wilker et al., *Propellants Explos. Pyrotech.*, 2007, 32, 135-148 describe that in particular Akardite II has shown favorable stabilizing properties. Another advantage is that Akardite II and its reaction products are known to be the least toxic of the conventional stabilizers. Like most other aromatic urea-derived stabilizers, Akardite II is typically produced via a precursor (e.g. a carbamoyl halide) that is obtained by reacting phosgene ($COCl_2$) with a corresponding amine. Since phosgene is highly toxic, a production process with this chemical requires extensive safety measures. It is therefore desirable to have a method for the production of aromatic urea derived stabilizers without requiring phosgene, e.g. by using a phosgene surrogate.

A suitable alternative for phosgene may be for instance dimethyl carbonate. An example is provided by Fu et al. in *Catalysis Communications* 2009, 10, 665-668 who describe a reaction of an N-heterocyclic moiety with dimethyl carbonate catalyzed by ionic liquids (i.e. the N-methylcarboxylation of N-heterocyclic compounds). Unfortunately, the non-heterocyclic amine (aniline) shows no reaction. It would be desirable to have a process where non-heterocyclic amines would react with compounds like dimethyl carbonate.

Wang Na et al. in *Petrochemical Technologies*, 2008, 1255-1259 describe the preparation of methyl N-phenyl carbamate of analine and dimethylcarbonate catalyzed by 1,1,3,3-tetramethylguanidine. The use of analine makes this reaction not suitable for the production of nitrocellulose stabilizers such as Akardite I and II.

It would desirable to provide a process wherein urea or carbamate compounds are prepared that can be used for the production of nitrocellulose stabilizers such as Akardite I and II.

The present inventors have surprisingly found a solution to at least one of these problems by preparing a compound according to formula I, in particular a carbamate or urea derivative according to formula I, comprising reacting an amine according to formula II and a carbonate or carbamate according to formula III, in the presence of a catalyst;

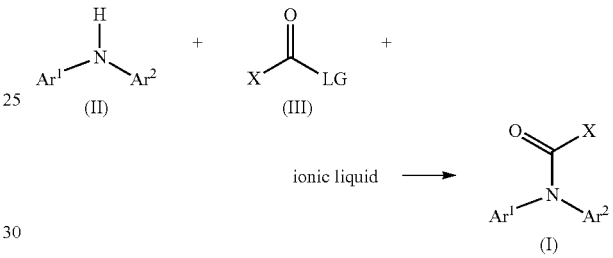

wherein
Ar$^1$ is an aryl that is optionally substituted with one or more halide, alkoxy, alkyl, nitro, sulfonate, ester, amide and/or carboxylate;
Ar$^2$ is Ar$^1$ or an aryl that is optionally substituted with one or more halide, alkoxy, alkyl, nitro, sulfonate, ester, amide, carboxylate;
X is an alkoxy, an aryloxy or an amine and is optionally substituted with one or more halide, alkoxy, alkyl, nitro, sulfonate, ester, amide and/or carboxylate;
LG is a leaving group.

It will be appreciated that because Ar$^1$ is an aryl, the present invention may be applicable to all aromatic urea derived stabilizers. It may further be appreciated that the carbonate or carbamate in accordance with formula III may be regarded as a phosgene surrogate, viz. it provides the carbonyl moiety present in the stabilizer.

The typical nitrocellulose-stabilizing compounds as described herein are ureas based on non-heterocyclic, secondary amines. Therefore, it is preferred that the amine according to formula II is a non-heterocyclic secondary amine. With non-heterocyclic secondary amine is meant any secondary amine of which the nitrogen atom of the amine is not present in a cycle.

For sake of clarity and conciseness, the carbamate or urea derivative according to formula I is herein also referred to as compound I, the amine according to formula II is herein also referred to as compound II, and the carbonate or carbamate according to formula III is herein also referred to as compound III.

It is preferred that the catalyst comprises an ionic liquid. An ionic liquid (IL) is a salt in the liquid state, typically salts whose melting point is relatively low, for instance 200° C. or less. The ionic liquid in accordance with the present invention may comprise a cation and an anion. Without wishing to be bound by theory, the inventors believe that when the cation comprises a proton which may form a hydrogen bond with the carbonyl of compound III, the reaction between compound II and III may be accelerated (i.e. catalyzed) by the ionic liquid. Said proton, which may be considered electron poor due to the electron withdrawing effect of the positively charged cation (preferably an imidazolium group), may therefore be regarded as being Lewis acidic. Therefore, the ionic liquid preferably comprises an electron poor hydrogen. Typically, the cation is an N,N-dialkyl imidazolium, preferably a 1-alkyl-3-methylimidazolium such as a 1-ethyl-methylimidazolium or a 1-butyl-3-methylimidazolium. Most preferably the cation is 1-butyl-3-methylimidazolium (BMIm).

Preferably, the anion of the ionic liquid is a small anion. It was found that smaller anions leads to better catalytic properties of the ionic liquid. Without wishing to be bound by theory, it is believed that the cation of the present invention is soft and that a harder anion results in weaker electrostatic bounding between the cation and anion. Such an effect is in general known by the "hard and soft Lewis acid and base" (HSAB) concept, also known as the Pearson acid base concept. Hence, a hard anion is preferred for the present invention. Small anions are typically hard anions. Therefore, the anion is preferably selected from the group consisting of hydroxide, chloride, bromide, iodate, acetate, hexafluorophosphate, tetrafluoroborate and combinations thereof. More preferably the anion is a hydroxide or a chloride.

Hence in view of the above, preferred ionic liquids are BMImCl, BMImOH or a combinations thereof.

In a particular embodiment, the catalyst comprises a non-nucleophilic base such that undesired side reactions of e.g. compound II with the base are limited. An example of such a base is N,N-diisopropylethylamine (DIPEA). Preferably a superbase is applied, yet more preferably an organic superbase is applied. Superbases are known in the art as compounds having a very high basicity. Suitable superbases can be found for instance in "Superbases for Organic Synthesis: Guanidines, Amidines, Phosphazenes and Related Organocatalysts" (Tsutomu Ishikawa; 2009; John Wiley & Sons, Ltd; ISBN: 978-0-470-51800-7). Superbase catalysts can be applied as solid-supported compounds. The organic superbase can be selected from the group consisting of amidines, phosphazenes, (poly)guanidines and or proton sponge type materials.

Phosphazenes that can be used for the present invention may be selected from the group consisting of tert-butyl-imino-tri(pyrrolidino)phosphorane (BTTP), tert-butylimino-tris(dimethylamino)phosphorane (t-Bu-$P_1$), 2-tert-butyl-imino-2-diethylamino-1,3-dimethylperhydro-1,3,2-diazaphosphorine (BEMP), tert-octylimino-tris(dimethylamino)phosphorane ($P_1$-t-Oct), tetramethyl(tris(dimethylamino)phosphoranylidene)phosphorictriamid-Et-imin ($P_2$-Et), 1-tert-butyl-2,2,4,4,4-pentakis(dimethylamino)-$2\lambda^5,4\lambda^5$-catenadi(phosphazene) ($P_2$-t-Bu), 1,1,1,3,3,3-hexakis(dimethylamino)diphosphazenium fluoride ($P_2$-F), tetrakis[tris(dimethylamino)phosphoranylidenamino]phosphonium fluoride ($P_5$-F), 1-tert-octyl-4,4,4-tris(dimethylamino)-2,2-bis[tris(dimethylamino)phosphoranylidenamino]-$2\lambda^5,4\lambda^5$-catenadi(phosphazene) ($P_4$-t-Oct) and 1-tert-butyl-4,4,4-tris(dimethylamino)-2,2-bis[tris(dimethylamino)-phosphoranylidenamino]-$2\lambda^5,4\lambda^5$-catenadi(phosphazene) ($P_4$-t-Bu).

A suitable guanidine is for instance a tetra-alkyl guanidine such as 1,1,3,3-tetramethylguanidine. Other examples of guanidines that could be selected for use in the present invention include 1,5,7-triazabicyclo[4.4.0]dec-5-ene (TBD), 7-methyl-1,5,7-triazabicyclo[4.4.0]dec-5-ene (MTBD), 7-ethyl-1,5,7-triazabicyclo[4.4.0]dec-5-ene (ETBD), 7-isopropyl-1,5,7-triazabicyclo[4.4.0]dec-5-ene (ITBD)

Examples of amidines that can be used for the present invention include vinamidines, formamidines, acetamidines, benzamidines, $EtN_2$-acetamidines, (poly)cyclic amidines, for instance 1,5-diazabicyclo[4.4.0]dec-5-ene (DBN), 3,3,6,9,9-pentamethyl-2,10-diazabicyclo[4.4.0]dec-1-ene (PM-DBD), 1,5-diazabicyclo[4.3.0]non-5-ene (DBN) and 1,8-diazabicyclo[5.4.0]undec-7-ene (DBU). Particularly good results have been obtained with DBU, so it is preferred that the catalyst comprises DBU.

Proton sponge type materials are known in the art to have at least two basic nitrogen atoms in their structure positioned such that one proton can be taken up resulting in a stabilized intramolecular hydrogen bond. Examples of proton sponge type materials that may be applied in the present invention include 1,8-Bis(dimethylamino)naphthalene (DMAN), 1,8-bis(hexamethyltriaminophosphazenyl)naphthalene (HMPN), 1,8-bis(tetramethylguanidino)naphthalene (TMGN).

It has further been found that the ionic liquid may be present in catalytic amounts. In this respect, with catalytic amounts is meant any amount which would be insufficient for the ionic liquid to be a solvent, e.g. a substoichiometric amount with respect to compound II, but the amount is still sufficient to acceptably catalyze the reaction. With substoichiometric amount is meant any molar amount that is less than the molar amount of compound II. A lower amount of ionic liquid may be beneficial for the purification of compound I and may also be economically attractive. A higher amount will result in a faster reaction. Therefore, the ionic liquid is preferably present in less than 50 mol %, more preferably less than 25 mol %, even more preferably less than 10 mol % and most preferably less than 5 mol %, for instance from 1 to 4 mol % with respect to compound II. The ionic liquid may be recycled, viz. it may be separated from the reaction mixture when the reaction is complete and may be re-used in a new reaction of compounds II and III.

It is known that in particular certain aromatic urea derived stabilizers are effective in stabilizing nitrocellulose. Therefore, it is preferable that $Ar^1$ is a phenyl that is optionally substituted with one or more halide, alkoxy, alkyl, nitro, sulfonate, ester, amide and/or carboxylate and $Ar^2$ is a phenyl or a $C_1$-$C_8$ alkyl and is optionally substituted with one or more halide, alkoxy, alkyl, nitro, sulfonate, ester, amide and/or carboxylate. More preferably, $Ar^1$ is phenyl and $Ar^2$ is phenyl or methyl such that compound II is e.g. methylphenylamine, more preferably wherein both $Ar^2$ and $Ar^1$ are phenyl such that compound II is diphenylamine.

In the context of the present invention, any alkyl may be linear or branched if possible. A $C_1$ alkyl consist of one carbon atom (i.e. a methyl), $C_4$ alkyl consist of four carbon atoms and may be linear or branched. $C_1$-$C_4$ alkyl means that the alkyl consists of one up to four carbon atoms. $C_1$-$C_8$ alkyl means that the alkyl consists of one up to eight carbon atoms.

In the reaction between compound II and III, the LG of compound III is replaced by the nitrogen of compound II and is therefore regarded as a leaving group. Typically, LG is an alkoxy, an aryloxy, an amine that is optionally substituted with one or two $C_1$-$C_4$ alkyl groups, an amide, a sulfonate such as tosylate, mesylate or nosylate, a halide, a nitrate, a phosphate and/or a carboxylate. Preferably, LG is a $C_1$-$C_4$ alkoxy or a $C_6$-$C_{10}$ aryloxy.

In a preferred embodiment the LG is X. This way compound III is a symmetrical compound which has shown to generally give good yields in the reaction between compounds II and III.

In another preferred embodiment, X is a $C_1$-$C_4$ alkoxy, an $C_6$-$C_{10}$ aryloxy or an amine optionally substituted with one or two $C_1$-$C_4$ alkyl groups. Preferably X is methoxy, ethoxy, tert-butoxy, phenoxy, amino (i.e. $NH_2$) or methylamine. More preferably X and LG are both methoxy or phenoxy. These groups have shown to give good reaction rates and yields.

It may be appreciated that in a particular embodiment of the present invention when compound III is O-methyl-N-methyl carbamate (i.e. X is NHMe and LG is OMe) and compound II is diphenyl amine (i.e. $Ar^2$ and $Ar^1$ are both phenyl), Akardite II may immediately be obtained. Compound III in accordance with this particular embodiment may for instance be obtained by the reaction of dimethylurea and dimethylcarbonate as is described in Shivarkar, A. B., S. P. Gupte, and R. V. Chaudhari, *J. Mol. Catal. A-Chem.*, 2004, 223, 85-92.

The inventors have found that the reaction compounds II and III may be influenced by the reaction temperature (i.e. the temperature at with compounds II and III are reacted). Preferably, the reaction temperature is at least 90° C., more preferably at least 125° C., for instance the reaction temperature is about 130° C. However, the reaction temperature may also be even higher than 130° C. as the reaction temperature may be dependent on LG and/or X. In a particular embodiment of the present invention, the temperature may be up to about 170° C. or higher. Generally the reaction temperature is below 200° C.

The inventors have further found that the ratio of compound II to compound III (calculated by dividing the molar amount of compound II by the molar amount of compound III and herein further referred to as the II/III ratio) may influence the yield of compound I. For instance, the reaction of diphenyl amine (i.e. compound II wherein $Ar^2$=$Ar^1$=Ph) and dimethyl carbonate (i.e. compound III wherein X=LG=OMe) at 90° C. for 24 h, gave a yield of O-methyl-N,N-diphenyl carbamate (i.e. a compound I) of 13% when the II/III ratio was 5. The corresponding yield was 18% when the II/III ratio was 10. The II/III ratio is therefore preferably at least 5, more preferably at least 10.

These observations may suggest that the reaction of compounds II and III into compound I is an equilibrium reaction. An equilibrium reaction has a forward and a reverse reaction. The inventors found that the yield be improved by countering the reverse reaction (i.e. the reaction of compound I into compounds II and III) by removal of the protonated LG that is liberated upon the formation of compound I. For instance, when LG is methoxy, the reaction of compounds II and III give methanol together to compound I. This methanol may react with formed compound I to form compounds II and III in the reverse reaction. Hence, in a preferred embodiment, the protonated LG that is also formed by the reaction of compound II and compound III is removed during the reaction. This may typically be effected by techniques such as evaporation, distillation, absorption, use of a membrane and the like. Preferably, the membrane is a semi-permeable membrane that is selectively permeable to LG-H and is thus not permeable to other reagents present in the reaction mixture.

In a particular embodiment of the present invention, typically when X is an alkoxy, e.g. methoxy, ethoxy or tert-butoxy or when X is an aryloxy, e.g. phenoxy, it is preferred that compound I is further converted into an urea. This is preferably effected by a conversion with an amine such as methylamine. As such a methyl-substituted urea may for instance be obtained. In a preferred embodiment, when $Ar^2$ and $Ar^1$ are both phenyl for compound I, this compound may further be converted into Akardite II, preferably by reacting compound I with methylamine.

Further converting compound I into an urea may simultaneously result in partial decomposition of compound I into and compound II. Without wishing to be bound by theory, this may proceed through a nucleophilic attack of the amine (e.g. methylamine) onto the carbonyl of compound I and subsequent leaving of compound II from the reactive intermediate and the formation of the corresponding carbamate or urea derivative. To obtain a higher overall yield, compound II resulting from the decomposition may be reused in a reaction with compound III. Hence, in a preferred embodiment, the resulting compound II is recycled back into the reaction of compound II and compound III. In such an embodiment, this compound II may be referred to as recycled compound II.

Hence, in a preferred embodiment, at least part of the total amount of compound II that is reacted to compound I is recycled compound II, i.e. compound II as obtained by the decomposition of compound I in its conversion into an urea as defined in the previous paragraph.

In a further preferred embodiment, the process of reacting compounds II and III into compound I and reacting compound I further into a urea is a continuous process. In such a process it is preferred that no intermediate purification of compound I is required.

A compound according to the present invention is thus a compound in accordance with formula I

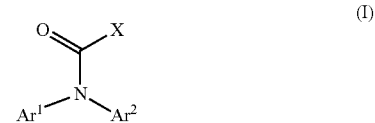

wherein $Ar^1$ is an aryl that is optionally substituted with one or more halide, alkoxy, alkyl, nitro, sulfonate, ester, amide and/or carboxylate;

$Ar^2$ is hydrogen, an aryl or an alkyl and optionally substituted with one or more halide, alkoxy, alkyl, nitro, sulfonate, ester, amide and/or carboxylate; and X is an alkoxy, aryloxy (such as phenoxy or derivatives thereof) or an amine and is optionally substituted with one or more halide, alkoxy, alkyl, nitro, sulfonate, ester, amide and/or carboxylate.

The compound in accordance with formula I (herein also referred to as compound I), may be prepared in accordance with the present invention. It may also be converted into a nitrocellulose-stabilizing compound such as Akardite II in accordance with the present invention.

In a preferred embodiment of compound I, $Ar^1$ is an aryl that is optionally substituted with one or more halide, alkoxy, alkyl, nitro, sulfonate, ester, amide and/or carboxylate and $Ar^2$ is an aryl or a $C_1$-$C_8$ alkyl and optionally substituted with one or more halide, alkoxy, alkyl, nitro, sulfonate, ester, amide and/or carboxylate, and X is a $C_1$-$C_4$ alkoxy, an $C_6$-$C_{10}$ aryloxy or an amine optionally substituted with one or two $C_1$-$C_4$ alkyl groups, preferably X is methoxy, ethoxy, tert-butoxy, phenoxy, amino or methylamine.

Preferably Ar$^1$ is phenyl, and Ar$^2$ is phenyl, methyl or ethyl and/or X is C$_1$-C$_4$ alkoxy or C$_6$-C$_{10}$ aryloxy, preferably Ar$^1$ is phenyl and Ar$^2$ is phenyl or methyl and/or X is methoxy or phenoxy, more preferably wherein both Ar$^1$ and Ar$^2$ phenyl.

Hence it may be appreciated that compound I is very suitable for use in the production of a nitrocellulose-stabilizing compound, in particular for use in the production of Akardite II. It may further be appreciated that urea compounds, in particular Akardite II readily crystallize from ethanol, which is also a suitable solvent for the formation of urea compounds, e.g. Akardite II, from compound I.

The present invention is further illustrated with a number of examples.

EXPERIMENTAL EXAMPLES

All chemicals were purchased from Sigma Aldrich and used without further purification. Nitrogen gas (N50) was purchased from Air Liquide. Water was obtained by the purification of tap water using a Mili-Q Direct-Q 5. Methylamine was purchased as a solution of 40 wt % in H$_2$O and 33 wt % in absolute ethanol. Ionic liquid BMImCl was dried in a vacuum stove (Heraeus vacuum oven, Thermo Scientific) at 100° C. for 3 hours and stored under N$_2$ atmosphere before use. Ace pressure tubes were purchased from Sigma Aldrich and fitted with a Teflex® O-ring, purchased from Eriks. Teflon tape was wrapped around the screw-thread of the pressure tube cap for extra grip. $^1$H and $^{13}$C NMR spectra were recorded on a Bruker Ascend 400 (400 MHz). Mass spectra were recorded on a Finnigan MAT900 using an electrospray ionization technique (ESI-MS), with methanol as the eluent. MS samples were prepared by dissolving a few milligrams of compound in HPLC-grade acetone. IR spectra were recorded on a PelkinElmer Spectrum Two FT-IR spectrometer.

Example 1

Synthesis of O-methyl-N,N-diphenyl Carbamate (Compound I, Wherein Ar$^2$=Ar$^1$=pH and X=OMe)

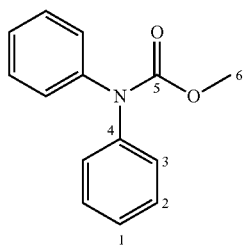 [SMILES: COC(=O)N(c1ccccc1)c1ccccc1]

In a round-bottomed flask (3-neck, 50 ml, fitted with reflux equipment and a valve), the ionic liquid BMImCl (0.5 mmol, 88 mg), diphenyl amine (5.0 mmol, 0.85 g) and anhydrous dimethyl carbonate (5 ml) were mixed under an N$_2$ atmosphere. The mixture was heated to 130° C. and stirred for 7 hours, while allowing the alcoholic reaction product to escape through the opened valve. It was then cooled to room temperature, the solvent was evaporated and the resulting crude product was purified on a SiO$_2$ column (the eluent was a mixture of ethyl acetate (EtOAc) and petroleum ether (PetEt):EtOAc/PetEt 10:90). The pure product was obtained as a colorless liquid, which crystallized quickly into a white solid when pressurized air was passed over the liquid. O-methyl-N,N-diphenyl carbamate was obtained in a yield of 80%.

$^1$H NMR (CDCl$_3$): δ 7.40-7.35 (m, 4H, 2 or 3), 7.30-7.22 (m, 6H, 1 and 2 or 3), 3.78 (s, 3H, 6).

$^{13}$C NMR: δ 155.31 (5), 142.59 (4), 128.95 (1, 2, or 3), 126.95 (1, 2, or 3), 126.18 (1, 2, or 3), 53.14 (6).

(ESI)-MS (calc.): 250.0 (250.3, [M-Na]$^+$) 282.1 (282.3, [M-Na-MeOH]$^+$, 308.0 (308.4, [M-Na-Me$_2$CO]$^+$, 475.2 (475.6, [M$_2$-Na]$^+$).

IR (cm$^{-1}$): 3100-3000 (w, C—H stretch, Ph), 2900-3000 (w, C—H stretch, CH$_3$), 1708 (s, C=O stretch, NC(=O)N), 1588, 1492 and 1439 (m, C=C stretch, Ph).

Example 2

Synthesis of O-ethyl-N,N-diphenyl Carbamate (Compound I, Wherein Ar$^1$=Ar$^2$=pH and X=OEt)

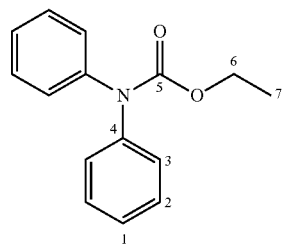 [SMILES: CCOC(=O)N(c1ccccc1)c1ccccc1]

Example 1 was repeated, only diethyl carbonate (5 ml) was used instead of dimethyl carbonate (5 ml). O-Ethyl-N,N-diphenyl carbamate was obtained in a yield of 57%.

$^1$H NMR (CDCl$_3$): δ 7.39-7.33 (m, 4H, 2 or 3), 7.28-7.20 (m, 6H, 1 and 2 or 3), 4.26 (q, 2H, 6), 1.27 (t, 3H, 7).

$^{13}$C NMR (CDCl$_3$): δ 154.86 (5), 142.70 (4), 128.87 (1, 2, or 3), 126.98 (1, 2, or 3), 126.01 (1, 2, or 3), 62.06 (6), 14.47 (7).

(ESI)-MS (calc.): 242.1 (242.3, [M-H]$^+$), 264.1 (264.3, [M-Na]$^+$), 296.1 (296.3, [M-Na-MeOH]$^+$), 322.0 (322.4, [M-Na-Me$_2$CO]$^+$), 505.2 (505.6, [M$_2$-Na]$^+$).

IR (cm$^{-1}$): 3100-3000 (w, C—H stretch, Ph), 3000-2900 (w, C—H stretch, CH$_2$, CH$_3$), 1715 (s, C=O stretch, NC(=O)O), 1590, 1491 and 1465 (m, C=C stretch, Ph).

Example 3

Synthesis of O-phenyl-N,N-diphenyl Carbamate (Compound I, Wherein Ar$^1$=Ar$^2$=pH and X=OPh)

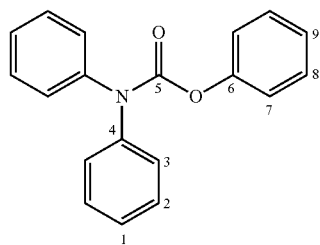 [SMILES: O=C(Oc1ccccc1)N(c1ccccc1)c1ccccc1]

Example 1 was repeated, only diphenyl carbonate (7.5 mmol, 1.61 g) was used instead of dimethyl carbonate (5 ml). O-Phenyl-N,N-diphenyl carbamate was obtained in a yield of 9%.

$^1$H NMR (CDCl$_3$): δ 7.439-7.34 (m, 9H), 7.31-7.15 (m, 6H)

$^{13}$C NMR (CDCl$_3$): δ 153.12 (5), 151.12 (6), 142.28 (4), 129.26 (2 or 8), 129.06 (2 or 8), 126.91 (1 or 9), 126.48 (1 or 9), 125.50 (3), 121.52 (7).

Example 4

Influence of Reaction Temperature on Formation of O-methyl-N,N-diphenyl Carbamate (Compound I, Wherein Ar$^1$=Ar$^2$=pH and X=OMe)

To investigate the influence of temperature on the reaction of compounds II and III, experiments according to example 1 were performed, with the only difference that the mixture was heated to different temperatures and stirred for different time periods. The experiments gave the following results.

heated to 90° C. for 24 h: 18% yield
heated to 110° C. for 7 h: 55% yield
heated to 130° C. for 7 h: 80% yield
heated to 130° C. for 16 h: 84% yield

Example 5

Synthesis of N-methyl-N',N'-diphenylurea (Akardite II)

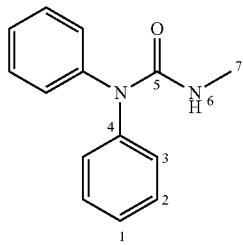 [SMILES: CNC(=O)N(c1ccccc1)c1ccccc1]

A solution of methylamine (MMA) in EtOH/H$_2$O in a ratio of 3:1 was prepared by mixing 3.5 ml of 33 wt % MMA in EtOH and 10.5 ml of 40 wt % MMA in H$_2$O. The freshly prepared MMA solution was mixed with O-methyl-N,N-diphenyl carbamate (2.0 mmol, 0.45 g) in a pressure tube (21 ml, fitted with Teflex® O-ring). After sealing the tube, the reaction mixture was heated to 100° C. and stirred until the carbamate was completely consumed. This occurred overnight. The reaction mixture was then cooled to room temperature, and the tube was left open to allow MMA to evaporate. Next, the solvent was evaporated, which turned the reaction mixture into an emulsion. EtOAc was added and the two phases were separated. The aqueous phase was washed with EtOAc. Both EtOAc solutions were combined and the solvent was evaporated. The contents of the resulting liquid were separated using a SiO$_2$ column (eluent: EtOAc/PetEt 25:75). The AK II fractions were combined and the solvent was evaporated. The remaining solid was washed with PetEt and pure Akardite II was obtained as a white solid in a yield of 17 mg, i.e. 3.8%.

$^1$H NMR (CDCl$_3$): δ 7.36-7.32 (m, 4H, 2 or 3), 7.30-7.20 (m, 6H, 1 and 2 or 3), 4.51 (s, 1H, 6), 2.84 (s, 3H, 7).

$^{13}$C NMR: 156.82 (5), 142.90 (4), 129.37 (1, 2, or 3), 127.42 (1, 2, or 3), 126.12 (1, 2, or 3), 27.48 (7).

(ESI)-MS (calc.): 227.1 (227.3, [M-H]$^+$), 249.1 (249.3, [M-Na]$^+$), 281.1 (281.3, [M-Na-MeOH]$^+$), 307.1 (307.4, [M-Na-Me$_2$CO]$^+$), 475.2 (475.6, [M$_2$-Na]$^+$).

IR (cm$^{-1}$): 3339 (m, N—H stretch, H—NMe), 3100-3000 (w, C—H stretch, Ph), 3000-2900 (w, C—H stretch, CH$_3$), 1653 (s, C=O stretch, NC(=O)N), 1587, 1486 and 1449 (m, C=C stretch, Ph), 1512 (N—H bend, H—NMe).

Example 6

Synthesis of N-methyl-N',N'-diphenylurea (Akardite II)

Example 5 was repeated, only O-ethyl-N,N-diphenyl carbamate (2.0 mmol, 0.48 g) was used instead of O-methyl-N,N-diphenyl carbamate. In this particular example, the carbamate was completely consumed during 12 days of stirring at 100° C. Akardite II was obtained in a yield of 17 mg, i.e. 3.8%.

Example 7

Synthesis of N-methyl-N',N'-diphenylurea (Akardite II)

O-Phenyl-N,N-diphenyl carbamate (0.35 mmol, 100 mg) was dissolved in 2 mL of MMA solution, 33 wt % in absolute ethanol. The mixture was stirred at room temperature for 2 days. Next, the solvent was evaporated. The contents of the resulting liquid were separated using a SiO$_2$ column (eluent: EtOAc/PetEt 25:75). The AK II fractions were combined and the solvent was evaporated. The remaining solid was washed with PetEt and pure Akardite II was obtained as a white solid in a yield of 54 mg, i.e. 68%.

Example 8

Synthesis of N-methyl-N',N'-diphenylurea (Akardite II)

Example 7 was repeated, only the reaction mixture was stirred for 5 days instead of 2 days. Akardite II was obtained as a white solid in a yield of 64 mg, i.e. 81%.

Example 9

Synthesis of O-methyl-N,N-diphenyl Carbamate (Compound I, Wherein Ar$^1$=Ar$^2$=pH and X=OMe)

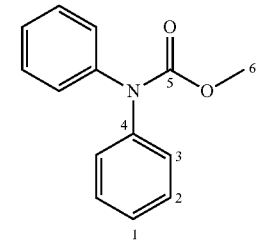 [SMILES: COC(=O)N(c1ccccc1)c1ccccc1]

In a round-bottomed flask (3-neck, 50 ml, fitted with reflux equipment and a valve), 'superbase' 1,8-diazabicyclo [5.4.0]undec-7-ene DBU (0.5 mmol, 88 mg), diphenyl amine (5.0 mmol, 0.85 g) and anhydrous dimethyl carbonate (5 ml). The mixture was heated to 130° C. and stirred for 7 hours, while allowing the alcoholic reaction product to escape through the opened valve. It was then cooled to room temperature, the solvent was evaporated and the resulting crude product was purified on a SiO$_2$ column (the eluent was a mixture of ethyl acetate (EtOAc) and petroleum ether (PetEt):EtOAc/PetEt 10:90). The pure product was obtained as a colorless liquid, which crystallized quickly into a yellowish solid when pressurized air was passed over the liquid. The solid was washed with diethyl ether (Et$_2$O). O-methyl-N,N-diphenyl carbamate was obtained in a yield of 11%.

The invention claimed is:

1. A method for preparing an N,N-diaryl substituted urea derivative for nitrocellulose stabilization, said method comprising a first step of preparing a carbamate according to formula I, comprising reacting an amine according to formula II and a compound according to formula III, in the presence of a catalyst that comprises an N,N-dialkylimidazolium ionic liquid or a non-nucleophilic base

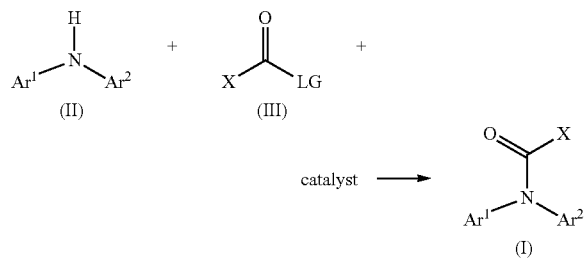

wherein
Ar$^1$ is an aryl that is optionally substituted with one or more of halide, alkoxy, alkyl, nitro, sulfonate, ester, amide and/or carboxylate;
Ar$^2$ is Ar$^1$ or an aryl that is optionally substituted with one or more of halide, alkoxy, alkyl, nitro, sulfonate, ester, amide and/or carboxylate;
X is an alkoxy, or an aryloxy and is optionally substituted with one or more of halide, alkoxy, alkyl, nitro, sulfonate, ester, amide and/or carboxylate; and
LG is an alkoxy, an aryloxy, an amine that is optionally substituted with one or two C$_1$-C$_4$ alkyl groups, an amide, a sulfonate, a halide, a nitrate, a phosphate or a carboxylate;
wherein the catalyst is present in less than 50 mol % with respect to the amine according to formula II; and
followed by a second step wherein the carbamate according to formula I is reacted with an amine to form said N,N-diaryl substituted urea derivative for nitrocellulose stabilization.

2. The method according to claim 1, wherein the catalyst comprises an N,N-dialkylimidazolium ionic liquid.

3. The method according to claim 2, wherein the ionic liquid comprises a cation and an anion and wherein the cation is a N,N-dialkyl imidazolium, and the anion is selected from the group consisting of hydroxide, chloride, bromide, iodate, acetate, hexafluorophosphate, tetrafluoroborate and combinations thereof.

4. The method according to claim 1, wherein the catalyst comprises a non-nucleophilic base.

5. The method according to claim 1, wherein Ar$^1$ is a phenyl, optionally substituted with one or more of halide, alkoxy, nitro, sulfonate, ester, amide, and carboxylate and Ar$^2$ is Ar$^1$ or a phenyl that is optionally substituted with one or more of halide, alkoxy, nitro, sulfonate, ester, amide, and/or carboxylate.

6. The method according to claim 1, wherein X is a C$_1$-C$_4$ alkoxy or a C$_6$-C$_{10}$ aryloxy.

7. The method according to claim 1, wherein the amine according to formula II and compound according to formula III are reacted at a temperature of at least 90° C.

8. The method according to claim 1, wherein the reaction between the amine according to formula II and the compound according to formula III also forms a protonated LG product and the protonated LG product is removed during said reaction.

9. The method according to claim 1, wherein the amine reacted with the carbamate according to formula I in the second step is ammonia or methylamine.

10. The method according to claim 1, wherein the carbamate according to formula I is converted into —N-methyl-N',N'-diphenylurea (Akardite II), wherein Ar$^1$ and Ar$^2$ are both phenyl and X is —NHMe.

11. The method according to claim 4, wherein the non-nucleophilic base is a superbase selected from the group consisting of amidines, phosphazenes, and guanidines.

12. The method according to claim 3, wherein the cation is 1-ethyl-3-methylimidazolium or 1-butyl-3-methylimidazolium (BMIm).

13. The method according to claim 3, wherein the anion is a hydroxide or a chloride.

14. The method according to claim 5, wherein both Ar$^1$ and Ar$^2$ are phenyl such that the amine according to formula II is diphenylamine.

15. The method according to claim 1, wherein the catalyst is present in less than 25 mol % with respect to the amine according to formula II.

16. The method according to claim 1, wherein the catalyst is present in less than 10 mol % with respect to the amine according to formula II.

* * * * *